US011896332B2

(12) United States Patent
Seow et al.

(10) Patent No.: US 11,896,332 B2
(45) Date of Patent: Feb. 13, 2024

(54) ROBOTIC SURGICAL ASSEMBLIES AND SURGICAL INSTRUMENT HOLDERS THEREOF

(71) Applicant: Covidien LP, Mansfield, MA (US)

(72) Inventors: Chi Min Seow, Watertown, MA (US); Mark Macleod, Brookfield, CT (US); Michael Zemlok, Prospect, CT (US)

(73) Assignee: COVIDIEN LP, Mansfield, MA (US)

( * ) Notice: Subject to any disclaimer, the term of this patent is extended or adjusted under 35 U.S.C. 154(b) by 215 days.

(21) Appl. No.: 17/466,358

(22) Filed: Sep. 3, 2021

(65) Prior Publication Data

US 2021/0393352 A1 Dec. 23, 2021

Related U.S. Application Data

(63) Continuation of application No. 16/073,474, filed as application No. PCT/US2017/016769 on Feb. 7, 2017, now Pat. No. 11,109,926.

(Continued)

(51) Int. Cl.
*A61B 34/37* (2016.01)
*A61B 90/50* (2016.01)
(Continued)

(52) U.S. Cl.
CPC .............. *A61B 34/37* (2016.02); *A61B 17/29* (2013.01); *A61B 34/30* (2016.02); *A61B 50/20* (2016.02);
(Continued)

(58) Field of Classification Search
CPC ......... A61B 50/20; A61B 90/50; A61B 34/30; A61B 34/37; A61B 34/71; A61B 2017/004477; A61B 2034/301
See application file for complete search history.

(56) References Cited

U.S. PATENT DOCUMENTS 5,460,062 A * 10/1995 Wilson, Jr. .............. B25B 13/48
81/57.3
6,923,613 B2 8/2005 Stuyt
(Continued)

FOREIGN PATENT DOCUMENTS

WO 2012104785 A1 8/2012
WO 2013159933 A1 10/2013
WO 2015167808 A1 11/2015

OTHER PUBLICATIONS

1 European Office Action dated Mar. 22, 2023 corresponding to counterpart Patent Application EP 17 753 648.9.
(Continued)

*Primary Examiner* — Martin T Ton
(74) *Attorney, Agent, or Firm* — Carter, DeLuca & Farrell, LLP

(57) ABSTRACT

A surgical instrument holder includes a carriage and a drive coupler. The carriage is configured for movable engagement to a surgical robotic arm. The drive coupler includes an outer member and a first gear rotatably disposed therein. The outer member extends from the carriage and defines a lateral slot configured for lateral receipt of a surgical instrument. The first gear defines a lateral slot and is rotatable within the outer member to a first position, in which the lateral slot of the first gear is in alignment with the lateral slot of the outer member such that a surgical instrument is receivable within the drive coupler through the lateral slots of the outer member and the first gear.

18 Claims, 6 Drawing Sheets

Related U.S. Application Data

(60) Provisional application No. 62/295,815, filed on Feb. 16, 2016.

(51) Int. Cl.
- *A61B 34/30* (2016.01)
- *A61B 50/20* (2016.01)
- *A61B 17/29* (2006.01)
- *A61B 17/00* (2006.01)

(52) U.S. Cl.
CPC .... *A61B 90/50* (2016.02); *A61B 2017/00398* (2013.01); *A61B 2017/00477* (2013.01)

(56) References Cited

U.S. PATENT DOCUMENTS

| | | | |
|---|---|---|---|
| 6,991,627 | B2 | 1/2006 | Madhani et al. |
| 7,204,844 | B2 | 4/2007 | Jensen et al. |
| 8,828,023 | B2 | 9/2014 | Neff et al. |
| 11,109,926 | B2 | 9/2021 | Seow et al. |
| 2002/0087166 | A1 | 7/2002 | Brock et al. |
| 2008/0134841 | A1* | 6/2008 | Wilson ............... B25B 13/481 81/57.33 |
| 2010/0318101 | A1 | 12/2010 | Choi |
| 2012/0116416 | A1 | 5/2012 | Neff et al. |
| 2013/0123783 | A1 | 5/2013 | Marczyk et al. |
| 2014/0257333 | A1* | 9/2014 | Blumenkranz ........ A61B 34/74 606/130 |
| 2015/0073339 | A1* | 3/2015 | Pacheco ............. A61M 25/0113 604/95.01 |
| 2015/0090057 | A1* | 4/2015 | Pacheco .................. F16H 19/02 74/25 |
| 2015/0327938 | A1* | 11/2015 | Bencteux ............... A61B 34/77 606/130 |
| 2017/0049519 | A1* | 2/2017 | Grover .................. A61B 34/35 |

OTHER PUBLICATIONS

European Search Report dated Feb. 22, 2018, corresponding to European Application No. 15785563.6; 7 pages.
International Search Report dated Jul. 9, 2015, corresponding to International Application No. PCT/US2015/026057; 4 pages.
European Search Report dated Oct. 7, 2019, corresponding to European Application No. 17753648.9; 10 pages.
Chinese Office Action with English translation, dated Jul. 13, 2020, corresponding to counterpart Chinese Application No. 201780009941.3; 19 total pages.
Chinese Office Action dated Mar. 2, 2021, issued in corresponding Chinese Appln. No. 201780009941, 8 pages.

* cited by examiner

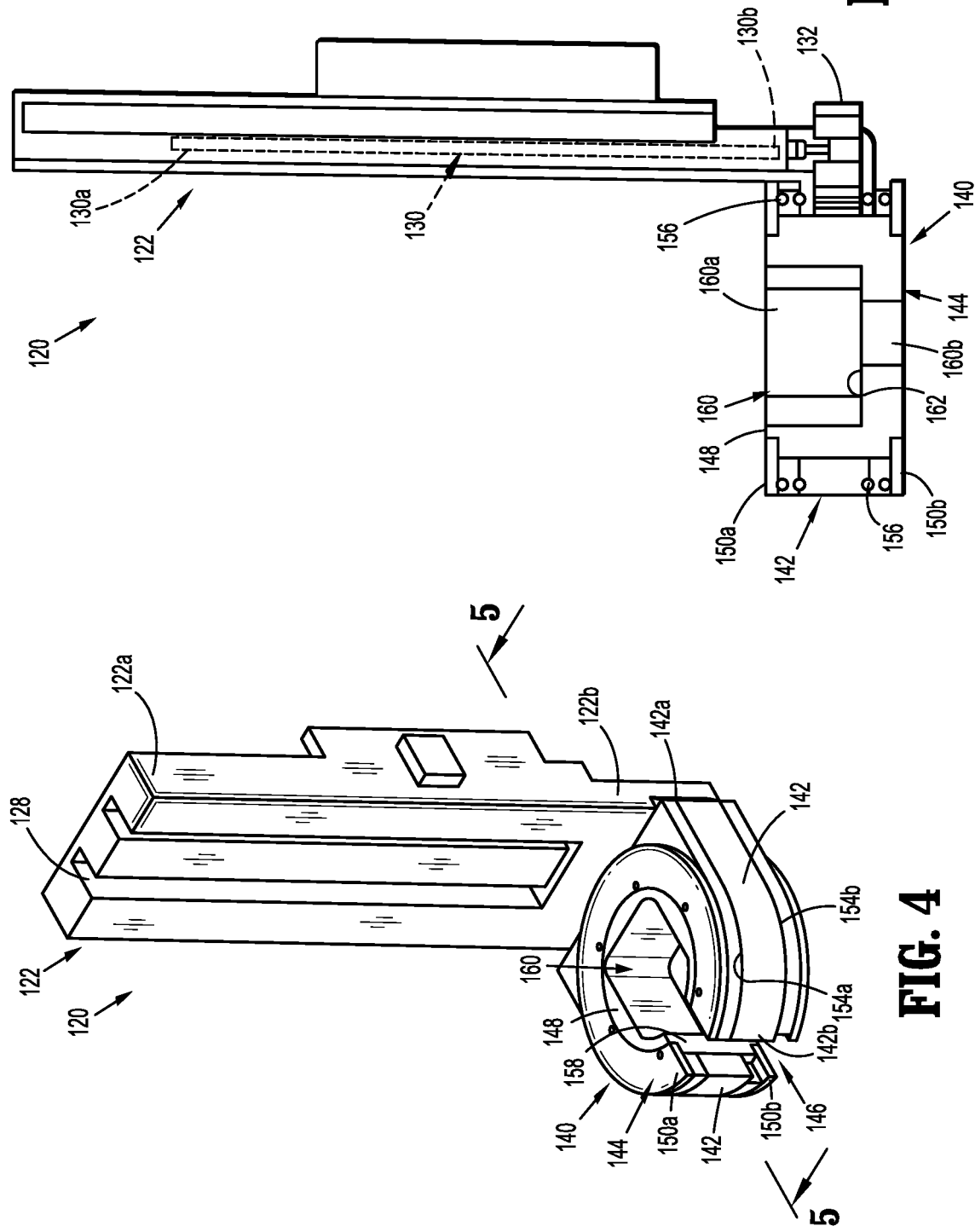

ROBOTIC SURGICAL ASSEMBLIES AND SURGICAL INSTRUMENT HOLDERS THEREOF

CROSS-REFERENCE TO RELATED APPLICATIONS

This application is a Continuation Application of U.S. patent application Ser. No. 16/073,474 filed on Jul. 27, 2018, which is a National Stage Entry of PCT/US2017/016769 filed on Feb. 7, 2017, which claims the benefit of and priority to U.S. Provisional Patent Application No. 62/295,815 filed on Feb. 16, 2016, the entire contents of each of which are incorporated by reference herein.

BACKGROUND

Robotic surgical systems have been used in minimally invasive medical procedures. Some robotic surgical systems include a console supporting a surgical robotic arm and a surgical instrument, having at least one end effector (e.g., forceps or a grasping tool), mounted to the robotic arm. The robotic arm provides mechanical power to the surgical instrument for its operation and movement. Each robotic arm may include an instrument drive unit that is operatively connected to the surgical instrument.

Manually-operated surgical instruments often include a handle assembly for actuating the functions of the surgical instrument. However, when using a robotic surgical system, no handle assembly is typically present to actuate the functions of the end effector. Accordingly, to use each unique surgical instrument with a robotic surgical system, an instrument drive unit is used to interface with the selected surgical instrument to drive operations of the surgical instrument. In robotic surgical systems, a robot arm may be used to hold the surgical instrument. In some robotic surgical systems, the entire length of the elongate shaft of the surgical instrument must pass through a holder or other feature of the robot arm, thereby making the removal or exchange of the surgical instrument cumbersome.

Accordingly, a need exists for a robotic surgical system that permits more efficient and expeditious removal or exchange of a surgical instrument.

Further, a need exists for a robotic surgical system having improved and increased usability.

SUMMARY

In accordance with an aspect of the present disclosure, a surgical instrument holder is provided and includes a carriage and a drive coupler. The carriage is configured for movable engagement with a surgical robotic arm. The drive coupler includes an outer member extending from the carriage and a first gear rotatably disposed within the outer member. The outer member defines a lateral slot therein configured for lateral receipt of a surgical instrument. The first gear defines a lateral slot therein and is rotatable within the outer member to a first position, in which the lateral slot of the first gear is in alignment with the lateral slot of the outer member such that a surgical instrument is receivable within the drive coupler through the lateral slots of the outer member and the first gear. A second gear is operably coupled with the first gear and configured to be drivingly rotated by an instrument drive unit to effect rotation of the first gear relative to the outer member.

In some embodiments, the drive coupler may further include a pair of gears spaced from one another and in meshing engagement with the first and second gears to transfer rotational motion from the second gear to the first gear. The lateral slot of the first gear has a width and the pair of gears may be spaced from one another a distance greater than the width of the lateral slot of the first gear.

It is contemplated that the first gear may be annular and have a plurality of teeth extending from a periphery thereof.

It is envisioned that the drive coupler may further include an inner member rotatably disposed within the outer member. The inner member has the first gear non-rotatably disposed therein. The inner member may define a counterbore therein configured for receipt of a surgical instrument therein. The counterbore may be in communication with the lateral slot of the first gear. The counterbore may include a first cavity and a second cavity in communication with the first cavity. The first cavity may be configured for non-rotatable receipt of a housing of a surgical instrument. The second cavity may be configured for receipt of a shaft of the surgical instrument.

In some aspects of the present disclosure, the first gear may have a passageway extending therethrough in communication with the lateral slot of the first gear. The passageway may be configured for receipt of a surgical instrument therein.

In some embodiments, the inner member may further include an upper plate supported on an upper surface of the outer member, and a lower plate supported on a lower surface of the outer member. The surgical instrument holder may further include bearings disposed between the upper plate of the inner member and the upper surface of the outer member, and the lower plate of the inner member and the lower surface of the outer member.

It is contemplated that the carriage may define a longitudinal track configured for slidable receipt of an instrument drive unit.

In another aspect of the present disclosure, a surgical assembly for use with a surgical robotic arm is provided. The surgical assembly includes a surgical instrument, an instrument drive unit, and a surgical instrument holder. The surgical instrument includes a housing, a shaft extending distally from the housing, and an end effector extending distally from the shaft. The instrument drive unit is configured for driving an actuation of the end effector of the surgical instrument. The surgical instrument holder includes a carriage and a drive coupler. The carriage has a first side configured for movable engagement with a surgical robotic arm, and a second side configured for engagement with the instrument drive unit. The drive coupler includes an outer member extending from the carriage, and a first gear rotatably disposed within the outer member. The outer member defines a lateral slot therein configured for lateral receipt of the shaft of the surgical instrument. The first gear defines a lateral slot therein and is rotatable within the outer member to a first position, in which the lateral slot of the first gear is in alignment with the lateral slot of the outer member such that the surgical instrument is receivable within the drive coupler through the lateral slots of the outer member and the first gear. A second gear is operably coupled to the first gear and configured to be drivingly coupled to the instrument drive unit such that actuation of the instrument drive unit rotates the second gear to effect rotation of the first gear relative to the outer member.

In some embodiments, the drive coupler may further include a pair of gears spaced from one another and in meshing engagement with the first and second gears to transfer rotational motion from the second gear to the first gear. The surgical instrument holder may further include a shaft having a first end configured to be drivingly coupled to the instrument drive unit, and a second end non-rotatably connected to the second gear.

It is envisioned that the drive coupler may further include an inner member rotatably disposed within the outer member. The inner member has the first gear non-rotatably disposed therein. The inner member may define a counterbore therein configured for receipt of the surgical instrument therein. The counterbore may be in communication with the lateral slot of the inner member. The counterbore may include a first cavity and a second cavity in communication with the first cavity. The first cavity may be configured for non-rotatable receipt of the housing of the surgical instrument. The second cavity may be configured for receipt of the shaft of the surgical instrument.

In some aspects of the present disclosure, the first gear may have a passageway extending therethrough in communication with the lateral slot of the first gear. The passageway may be configured for receipt of the shaft of the surgical instrument therein.

In another aspect of the present disclosure, another embodiment of a surgical instrument holder is provided and includes a carriage and a drive coupler. The carriage is configured for movable engagement to a surgical robotic arm. The drive coupler includes an outer member, an annular member, first and second pulleys, and a belt. The outer member extends from the carriage and defines a lateral slot therein configured for lateral passage of a surgical instrument. The annular member defines a lateral slot therein and is rotatable within the outer member to a first position. In the first position, the lateral slot of the annular member is in alignment with the lateral slot of the outer member such that a surgical instrument is receivable within the drive coupler through the lateral slots of the outer member and the annular member. The first and second pulleys are spaced from one another and are disposed adjacent the annular member. The belt is disposed about the first and second pulleys and in engagement with the annular member. The first pulley and/or the second pulley are configured to be drivingly rotated to rotate the belt to effect rotation of the annular member relative to the outer member.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about + or − 10 degrees from true parallel and true perpendicular.

BRIEF DESCRIPTION OF THE DRAWINGS

Embodiments of the present disclosure are described herein with reference to the accompanying drawings, wherein:

FIG. 4 is a perspective view of a surgical instrument holder of the surgical assembly of FIG. 2;

FIG. 5 is a cross sectional view, taken along line 5-5 in FIG. 4, of the surgical instrument holder;

DETAILED DESCRIPTION

Figure 1:
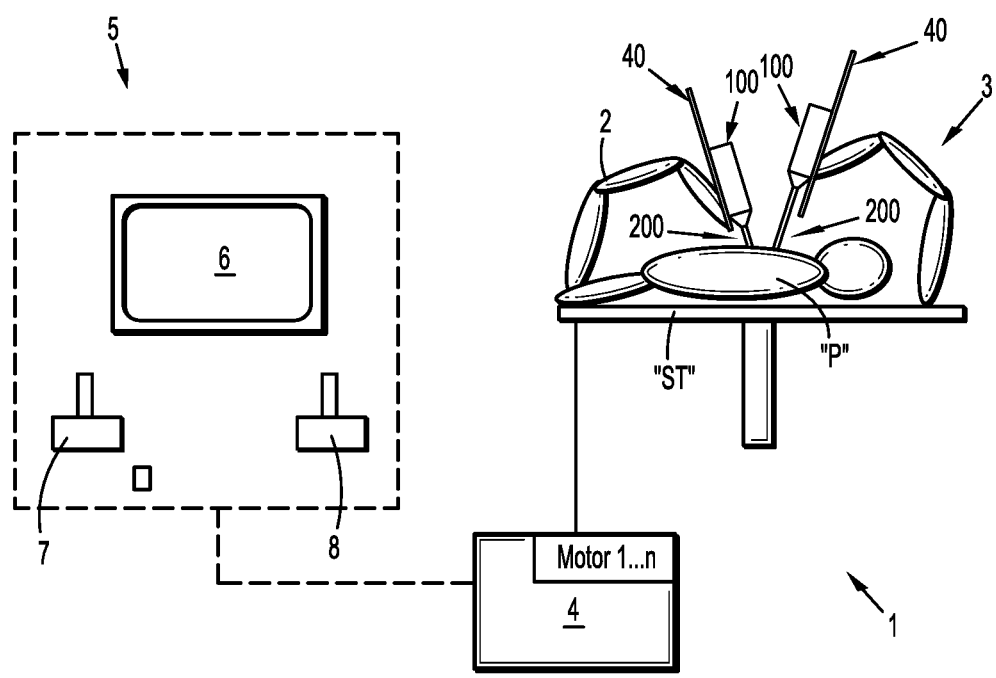
FIG. 1 is a schematic illustration of a robotic surgical system including a robotic surgical assembly in accordance with the present disclosure.

Embodiments of the presently disclosed surgical assembly including an instrument drive unit, a surgical instrument, and a surgical instrument holder, and methods thereof, are described in detail with reference to the drawings, in which like reference numerals designate identical or corresponding elements in each of the several views. As used herein the term "distal" refers to that portion of the surgical instrument holder, surgical instrument, and/or instrument drive unit that is closer to the patient, while the term "proximal" refers to that portion of the surgical instrument holder, surgical instrument, and/or instrument drive unit that is farther from the patient.

Referring initially to FIG. 1, a surgical system, such as, for example, a robotic surgical system 1, generally includes a plurality of surgical robotic arms 2, 3 having a robotic surgical assembly 100 including an electromechanical surgical instrument 200 removably attached to a slide rail 40 of surgical robotic arms 2, 3; a control device 4; and an operating console 5 coupled with control device 4.

Operating console 5 includes a display device 6, which is set up in particular to display three-dimensional images; and manual input devices 7, 8, by means of which a person (not shown), for example a surgeon, is able to telemanipulate robotic arms 2, 3 in a first operating mode, as known in principle to a person skilled in the art. Each of the robotic arms 2, 3 may be composed of a plurality of members, which are connected through joints. Robotic arms 2, 3 may be driven by electric drives (not shown) that are connected to control device 4. Control device 4 (e.g., a computer) is set up to activate the drives, in particular by means of a computer program, in such a way that robotic arms 2, 3, the attached robotic surgical assembly 100, and thus electromechanical surgical instrument 200 (including an electromechanical end effector 210 (FIG. 2)) execute a desired movement according to a movement defined by means of manual input devices 7, 8. Control device 4 may also be set up in such a way that it regulates the movement of robotic arms 2, 3 and/or of the drives.

Robotic surgical system 1 is configured for use on a patient "P" lying on a surgical table "ST" to be treated in a minimally invasive manner by means of a surgical instrument, e.g., electromechanical surgical instrument 200. Robotic surgical system 1 may also include more than two robotic arms 2, 3, the additional robotic arms likewise being connected to control device 4 and being telemanipulatable by means of operating console 5. A surgical instrument, for example, electromechanical surgical instrument 200 (including the electromechanical end effector 210 (FIG. 2)), may also be attached to the additional robotic arm.

Control device 4 may control a plurality of motors, e.g., motors (Motor 1 . . . n), with each motor configured to drive movement of robotic arms 2, 3 in a plurality of directions. Further, control device 4 may control a plurality of motors (not shown) of an instrument drive unit 110 of robotic surgical assembly 100 that drive various operations of end effector 210 (FIG. 2) of electromechanical surgical instrument 200, and a rotation motor, such as, for example, a canister motor 112 (FIG. 2), configured to drive a relative rotation of electromechanical surgical instrument 200 along a longitudinal axis "X" (FIG. 2) thereof, as will be described in detail below. In embodiments, each motor of the instrument drive unit 110 can be configured to actuate a drive rod/cable or a lever arm to effect operation and/or movement of the electromechanical end effector 212 of electromechanical surgical instrument 200.

For a detailed discussion of the construction and operation of a robotic surgical system, reference may be made to U.S. Pat. No. 8,828,023, filed on Nov. 3, 2011, entitled "Medical Workstation," the entire contents of which are incorporated by reference herein.

Figure 2:
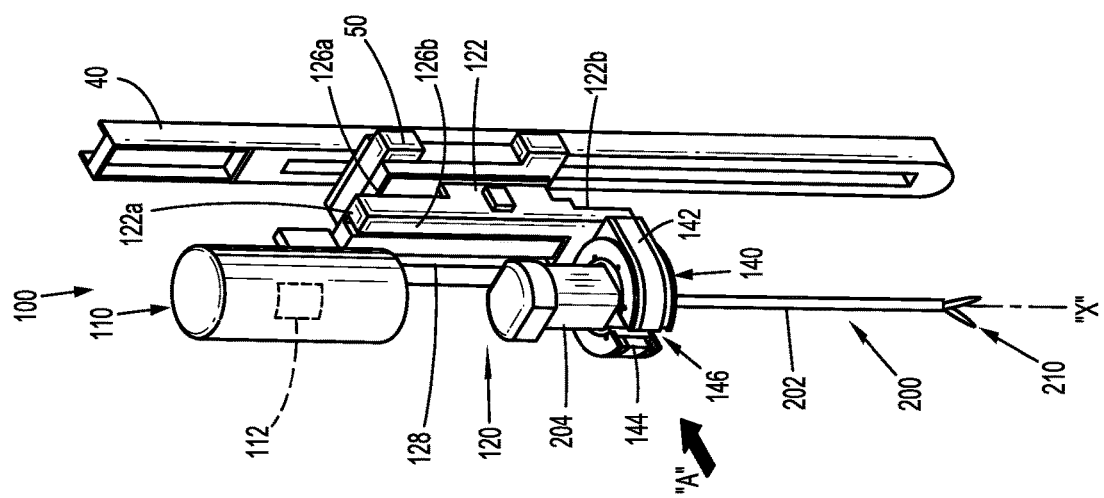
FIG. 2 is a perspective view, with parts separated, of the surgical assembly of FIG. 1.

With reference to FIGS. 1 and 2, robotic surgical system 1 includes the robotic surgical assembly 100 that is coupled with or to robotic arm 2 or 3. The robotic surgical assembly 100 includes instrument drive unit 110, a surgical instrument holder 120, and the electromechanical surgical instrument 200. Instrument drive unit 110 transfers power and actuation forces from its motors to driven members of electromechanical surgical instrument 200 to ultimately drive movement of components of the end effector 212 of electromechanical surgical instrument 200, for example, a movement of a knife blade (not shown) and/or a closing and opening of jaw members of the end effector 212, the actuation or firing of a stapler, and/or the activation or firing of an electrosurgical energy-based instrument, or the like. Instrument drive unit 110 is further configured to rotate electromechanical surgical instrument 200 about its longitudinal axis "X" by motor 112 (e.g., a fifth axis rotation motor) of instrument drive unit 110.

Turning now to FIGS. 2-6, surgical instrument holder 120 of surgical assembly includes a back member or carriage 122 and a drive coupler 140 extending perpendicularly from an end 122b of carriage 122. In some embodiments, drive coupler 140 may extend at various angles relative to carriage 122 and from various portions of carriage 122. Carriage 122 has a first side 126a and a second side 126b, opposite first side 126a. First side 126a of carriage 122 may be detachably connectable to a slide 50, which is slidably mountable to rail 40 of robotic arm 2. Alternately, first side 126a of carriage 122 may be permanently mounted with range/displacement limits. Second side 126b of carriage 122 defines a longitudinal track 128 configured for slidable receipt of instrument drive unit 110. Carriage 122 may support or house a motor (not shown) which receives controls and power from control device 4 to selectively move instrument drive unit 110 along longitudinal track 128. Carriage 122 has a rotatable shaft 130 (FIG. 5) extending longitudinally therethrough for interconnecting fifth motor 112 of instrument drive unit 110 to a plurality of inter-related gears 132, 170a, 170b, 164 (FIG. 6) in drive coupler 140 to effect a rotation of surgical instrument 200 about its longitudinal axis "X," as will be described in greater detail below. Alternatively, rotation motor 112 may be mechanically coupled to one of gears 132, 170a, or 170b in drive coupler 140.

Figure 3:
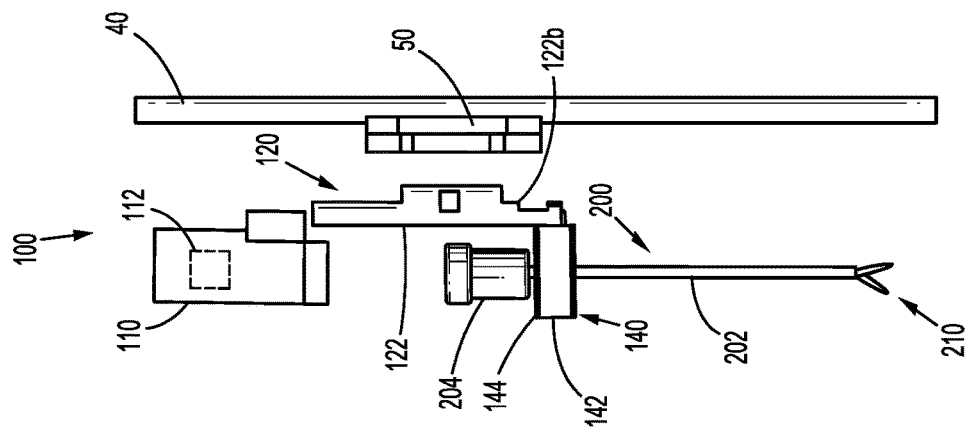
FIG. 3 is a side view of the surgical assembly of FIG. 2.

With reference to FIGS. 2 and 3, drive coupler 140 of surgical instrument holder 120 is configured to receive and hold surgical instrument 200 and effect rotation of surgical instrument 200 about its longitudinal axis "X," as will be described in detail below. Drive coupler 140 generally includes a C-shaped outer member 142 and an inner member 144 rotatably disposed within outer member 142. In some embodiments, outer member 142 may have features for positional clocking and may assume a variety of shapes, such as, for example, V-shaped, hook-shaped, or an asymmetrical form. Outer member 142 includes of a pair of arms each having an arcuate configuration. The arms each include a first end 142a fixedly engaged to end 122b of carriage 122, and a second free end 142b. Second ends 142b of the arms are spaced from one another to define a lateral slot 146 of outer member 142 configured for lateral receipt of a shaft 202 of surgical instrument 200. As such, surgical instrument 200 can be positioned within drive coupler 140 of surgical instrument holder 120 by moving surgical instrument 200 in a direction perpendicular to its longitudinal axis "X" and through lateral slot 146 of outer member 142.

With reference to FIGS. 4 and 5, inner member 144 of drive coupler 140 of surgical instrument holder 120 is configured to hold surgical instrument 200 and to cause surgical instrument 200 to rotate therewith. Inner member 144 includes an internal housing 148 and upper and lower plates 150a, 150b fixed to opposing sides of internal housing 148. Upper and lower plates 150a, 150b each have a c-shaped configuration and are supported on, or abut, an upper surface 154a and a lower surface 154b of outer member 142, respectively. Plates 150a, 150b of inner member 144 maintain internal housing 148 of inner member 144 within outer member 142 while permitting rotation of inner member 144 relative to outer member 142. A plurality of bearings 156, such as, for example, a split bushing or a recirculating ball bearing that has a split in the middle, are disposed between upper plate 150a of inner member 144 and upper surface 154a of outer member 142, and lower plate 150b of inner member 144 and lower surface 154b of outer member 142, to facilitate rotation of inner member 144 relative to outer member 142.

In some embodiments, upper and lower bearing journals or races (not shown) can be incorporated into inner member 144 to axially and radially support inner member 144, and which may be fabricated from any combination of metals, ceramics, or plastics.

Internal housing 148 of inner member 144 defines a lateral slot 158 therein for lateral passage of shaft 202 of surgical instrument 200 therethrough. Lateral slot 158 of inner member 144 has the same or substantially the same dimensions (e.g., width) as lateral slot 146 of outer member 142. As such, inner member 144 can be rotated relative to outer member 142 to a position in which lateral slot 158 of inner member 144 and lateral slot 146 of outer member 142 are in alignment. When lateral slots 146, 158 are in alignment, surgical instrument 200 can be laterally loaded into surgical instrument holder 120 or laterally unloaded from surgical instrument holder 120.

With specific reference to FIG. 5, internal housing 148 of inner member 144 further defines a counterbore 160 therein configured for receipt of housing 204 of surgical instrument 200 therein. Counterbore 160 includes a first cavity 160a and a second cavity 160b in communication with first cavity 160a. A bottom internal surface 162 of internal housing 148 that defines first cavity 160a of counterbore 160 is configured to support or seat housing 204 of surgical instrument 200 thereon when surgical instrument 200 is disposed within drive coupler 140 of surgical instrument holder 120. First cavity 160a of counterbore 160 has a non-circular configuration or profile (e.g., squared or D-shaped) corresponding to a non-circular outer configuration or profile of housing 204 of surgical instrument 200. In some embodiments, first cavity 160a of counterbore 160 may be round with clocking, or may be asymmetrical. In some embodiments, the depth of counterbore 160 of inner member 144 may be low to minimize the axial displacement required for loading and unloading of surgical instrument 200.

Upon seating housing 204 of surgical instrument 200 within first cavity 160a of counterbore 160, rotation of inner member 144 results in rotation of surgical instrument 200 since housing 204 of surgical instrument 200 is non-rotatably captured within first cavity 160a of counterbore 160. In some embodiments, housing 204 of surgical instrument 200 and first cavity 160a of counterbore 160 may be circular, and housing 204 of surgical instrument 200 may be non-rotatably disposed within first cavity 160a via a friction fit engagement or other various engagements.

Second cavity 160b of counterbore 160 is narrower than first cavity 160a and is configured for receipt of shaft 202 of surgical instrument 200. Second cavity 160b of counterbore 160 is in communication with lateral slot 158 of inner member 144 such that shaft 202 of surgical instrument 200 can be laterally received within second cavity 160b of counterbore 160 by being passed through lateral slot 158 of internal housing 148 of inner member 144.

In some embodiments, the motor that drives the rotation of inner member 144 may be local to inner member 144 or it may be displaced using a drive shaft, a flex shaft, or a belt. In some embodiments, the motor that drives the rotation of inner member 144 can incorporate mechanical or electrical brakes or a high back drive mechanism such as a worm drive for desired back drive torques or positional locking for critical modes of operation.

Figure 6:
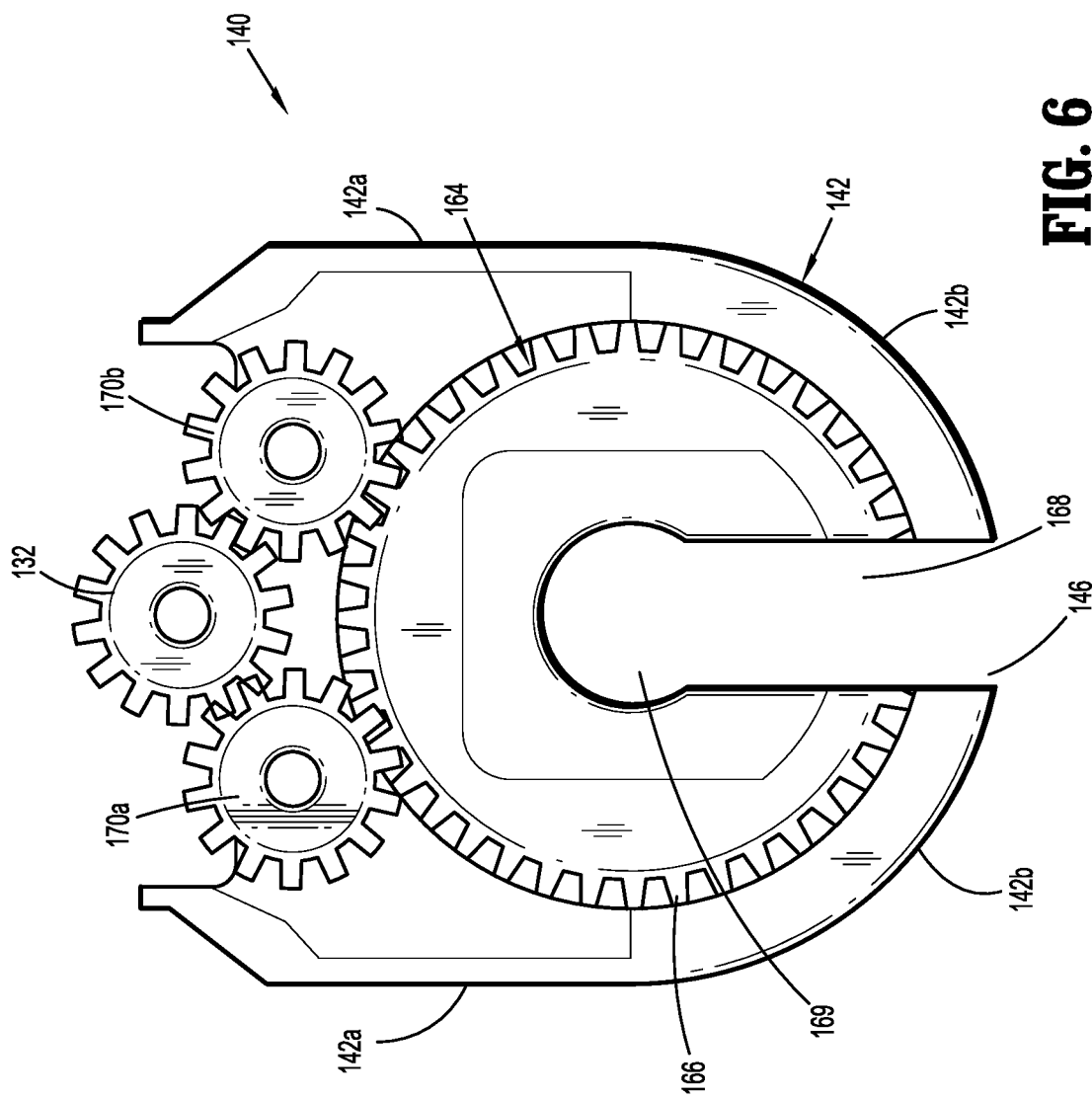
FIG. 6 is a top view, with parts removed, of a drive coupler of the surgical instrument holder of FIG. 4 illustrating a lateral slot of a first gear in alignment with a lateral slot of an outer member of the surgical instrument holder.

With reference to FIGS. 4-6, inner member 144 of drive coupler 140 further includes a first gear 164 embedded within (i.e., in non-rotatable engagement with) internal housing 148 of inner member 144 such that internal housing 148 of inner member 144 rotates with first gear 164 of inner member 144. First gear 164 has an annular shape and a plurality of gear teeth 166 extending radially from a periphery thereof. First gear 164 defines a lateral slot 168 therein, which is in fixed alignment with lateral slot 158 of inner member 144. First gear 164 further defines a central passageway 169, e.g., a circular passageway, extending therethrough in communication with lateral slot 168 of first gear 164. Upon seating surgical instrument 200 within inner member 144 of drive coupler 140, shaft 202 of surgical instrument 200 extends through passageway 169 of first gear 164. First gear 164 is in operable association with shaft 130 of carriage 122, which is driven by rotation motor 112, such that rotation of shaft 130 rotates first gear 164 to rotate inner member 144 relative to outer member 142, as will be described in greater detail below.

With specific reference to FIG. 6, drive coupler 140 of surgical instrument holder 120 further includes a pair of gears 170a, 170b, such as, for example, spur gears, disposed adjacent second end 122b of carriage 122 (FIG. 4). Both gears 170a, 170b are in meshing engagement with teeth 166 of first gear 164 to transfer rotational motion from a second gear 132 of shaft 130 to first gear 164. Gears 170a, 170b are spaced from one another a distance greater than the width of lateral slot 168 of first gear 164. Specifically, a point of engagement of gears 170a, 170b with first gear 164 is spaced from one another by a distance greater than an arcuate distance or length of lateral slot 168 of first gear 164 along an outer radial edge of first gear 164. In this way, as first gear 164 rotates within outer member 142 to a position in which lateral slot 168 of first gear 164 is radially aligned with one of gears 170a, 170b, or in any position relative to gears 170a, 170b, at least one of gears 170a, 170b will be in contact with first gear 164 such that the transfer of rotational motion from gears 170a, 170b to first gear 164 will be uninterrupted.

In some embodiments, gears 132, 170a, 170b, 164 of drive coupler 140, or any gear disclosed herein, may be spur gears, bevel gears, or miter gears, and may incorporate a helix or spiral profile to minimize noise and backlash.

In some embodiments, instead of having the pair of gears 170a, 170b, drive coupler 140 may be configured such that second gear 132 of shaft 130 may be in direct meshing engagement with first gear 164. In this embodiment, second gear 132 of shaft 130 has a diameter whereby an arc length of second gear 132 spans across the width of lateral slot 168 of first gear 164 so that second gear 132 always remains in contact with at least one tooth of first gear 164 irrespective of the position of first gear 164 relative to second gear 132.

In some embodiments, gear 164, or any suitable component of inner member 144, may incorporate an encoder, a magnet, a ferrous-containing optical target fabricated, that can be read by a corresponding sensor element (not shown) of slide 50. In some embodiments, gear 164, or any suitable component of inner member 144, may incorporate controls and/or firmware. When robotic surgical assembly 100 is in an initialization mode or in an instrument exchange mode, the controls and/or firmware may move gear 164, or any component of inner member 144, to position lateral slot 168 of gear 164 and/or lateral slot 158 of inner member 144 out of alignment with or perpendicular to lateral slot 146 of outer member 142.

As briefly mentioned above with respect to FIG. 5, surgical instrument holder 120 has a shaft 130 extending longitudinally through carriage 122 to operably interconnect the fifth motor 112 or an additional motor of instrument drive unit 110 and first gear 164 of drive coupler 140 of surgical instrument holder 120. Shaft 130 of surgical instrument holder 120 has a first end 130a configured to operably connect to motor 112 of instrument drive unit 110, and a second 130b end having second gear 132 non-rotatably disposed thereabout. As such, an actuation of motor 112 of instrument drive unit 110 effects rotation of shaft 130 and second gear 132 therewith. Rotation of second gear 132 rotates gears 170a, 170b, which in turn, rotates first gear 164 relative to and within outer member 142 of drive coupler 140.

In some embodiments, shaft 130 of surgical instrument holder 120 may incorporate an encoder or a rotational position sensor configured to sense a rotational position of lateral slot 168 of first gear 164. In some embodiments, the encoder may be disposed at any suitable location of surgical instrument holder 120. The encoder is readable to align first gear 164 of inner member 144 for any desired application and to confirm function. In some embodiments, shaft 130 of surgical instrument holder 120, or any suitable component of surgical instrument holder 120, may incorporate a gearhead (not shown) to provide additional torque or back drive loads to gear 164. In operation, prior to or during a surgical procedure, surgical instrument 200 may be coupled to robotic arm 2. In particular, instrument drive unit 110 may be moved, either manually or by actuating a motor within carriage 122 of surgical instrument holder 120, away from drive coupler 140 to a position toward a first end 122a of carriage 122, as shown in FIG. 2. The motor 112 of instrument drive unit 110 is actuated to drive rotation of shaft 130 of surgical instrument holder 120. Rotation of shaft 130 effects rotation of second gear 132, which is non-rotatably attached to second end 130b of shaft 130. Rotation of second gear 132, which is in meshing engagement with gears 170a, 170b, causes gears 170a, 170b to rotate. Rotation of gears 170a, 170b causes first gear 164 of drive coupler 140 to rotate relative to and within outer member 142. Actuation of the motor 112 of instrument drive unit 110 is continued until lateral slot 158 of inner member 144, and thus also lateral slot 168 of first gear 164, are in alignment with lateral slot 146 of outer member 142 to provide a pathway for shaft 202 of surgical instrument 200 to pass.

With instrument drive unit 110 spaced from drive coupler 140 of surgical instrument holder 120 and lateral slots 146, 168, 158 of drive coupler 140 in alignment with one another, surgical instrument 200 is moved in a lateral direction, as indicated by arrow "A" in FIG. 2, toward surgical instrument holder 120 to pass shaft 202 of surgical instrument 200 through lateral slots 146, 158 and into second cavity 160b of inner member 144 of drive coupler 140. Housing 204 of surgical instrument 200 may then be seated within first cavity 160a of inner member 144 of drive coupler 140 to non-rotatably dispose surgical instrument 200 with surgical instrument holder 120. Instrument drive unit 110 may then be translated toward housing 204 of surgical instrument 200 to operably couple drive couplers or sleeves (not shown) of instrument drive unit 110 with corresponding driven couplers or sleeves (not shown) of housing 204 of surgical instrument 200, and operably couple the motor(s) 112 of instrument drive unit 110 with surgical instrument 200.

With surgical instrument 200 disposed within surgical instrument holder 120 and operably connected to instrument drive unit 110, an actuation of a motor 112 of instrument drive unit 110 will rotate shaft 130 of surgical instrument holder 120 to rotate second gear 132. Rotation of second gear 132 results in a rotation of first gear 164 via gears 170a, 170b. As first gear 164 rotates, inner member 144 of drive coupler 140 rotates therewith and relative to outer member 142 to effect rotation of surgical instrument 200 about its longitudinal axis "X" and relative to surgical instrument holder 120. As such, a rotational position of end effector 210 of surgical instrument 200 may be selectively adjusted while surgical instrument 200 is held within surgical instrument holder 120.

Further, by having one of gears 170a, 170b in contact or in engagement with first gear 164 at all times, as first gear 164 is rotated and lateral slot 168 of first gear 164 radially aligns with gear 170a, gear 170b may continue to independently drive and rotate first gear 164. Likewise, when lateral slot 168 of first gear 164 radially aligns with gear 170b, gear 170a may continue to independently drive and rotate first gear 164. In this manner, first gear 164 (including lateral slot 168) may be rotated more than 360 degrees as needed to rotate surgical instrument 200 about its longitudinal axis "X."

To unload or remove surgical instrument 200 from surgical instrument holder 120, a motor 112 of instrument drive unit 110 is actuated to rotate inner member 144, including first gear 164, relative to outer member 142 until lateral slots 146, 168, 158 of drive coupler 140 are in alignment. Instrument drive unit 110 may then be translated away from housing 204 of surgical instrument 200 to disconnect surgical instrument 200 from instrument drive unit 110. With lateral slots 146, 168, 158 in alignment with one another and instrument drive unit 110 disconnected from surgical instrument 200, surgical instrument 200 can be removed from surgical instrument holder 120 by being moved laterally through lateral slots 146, 168, 158 and out of drive coupler 140 of surgical instrument holder 120.

Under certain circumstances in which power to instrument drive unit 110 is disrupted, surgical instrument 200 may be removed by manually moving instrument drive unit 110 away from housing 204 of surgical instrument 200 and surgical instrument 200 may be manually rotated until lateral slots 146, 168, 158 of drive coupler 140 are aligned with one another. Upon manually aligning lateral slots 146, 168, 158, surgical instrument 200 can be removed from surgical instrument holder 120 by being moved laterally through lateral slots 146, 168, 158 and out of drive coupler 140 of surgical instrument holder 120.

In some embodiments, inner member 144, or any component thereof, may be sterilized through autoclave, use of an ethylene oxide (ETO) process, use of peroxide, use of gamma radiation or be aseptically covered with a sterilized upper and lower cover. Inner member 144 may be fabricated from various metals, for example, steel, aluminum, and/or magnesium alloy, and may incorporate platings or coatings to prolong cleanability and wear. Inner member 144 may be made from various plastics, polymers, and/or ceramics, and may include drafting and/or elastomer interference features to minimize play and movement when loaded.

Figure 7:
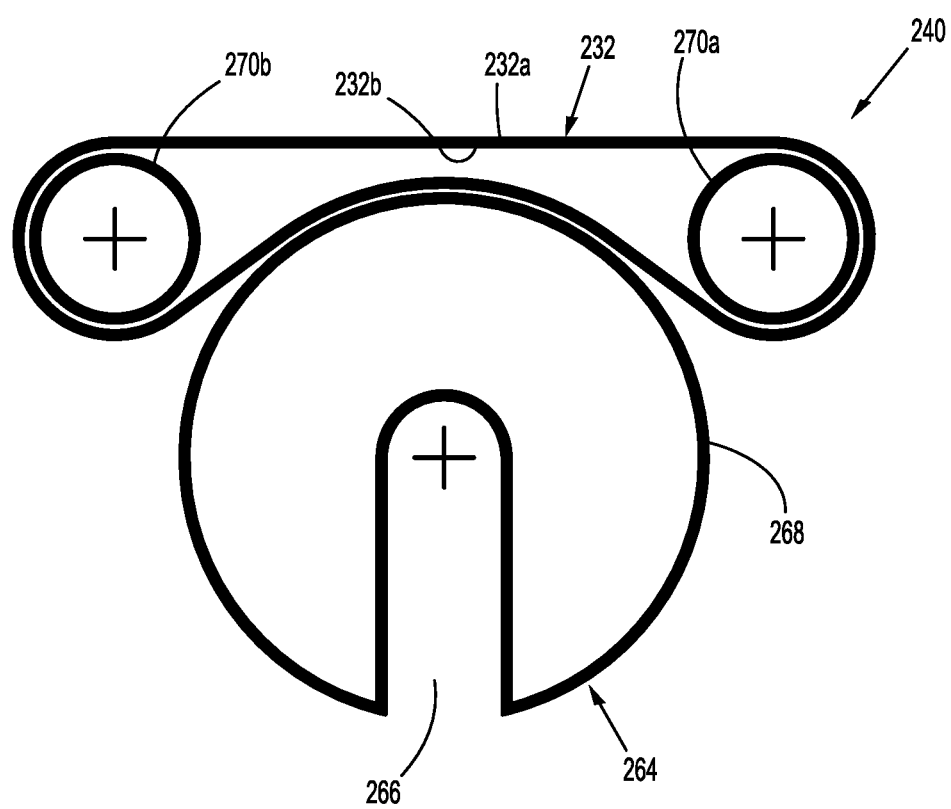
FIG. 7 is a top view of a pulley system configured to be incorporated into the surgical instrument holder of FIG. 4.

With reference to FIG. 7, another embodiment of a drive coupler 240 is provided, similar to drive coupler 140 described above with reference to FIG. 6. Drive coupler 240 differs from drive coupler 140 by replacing the gears 164, 170a, 170b, 132 of drive coupler 140 with a pulley system, as will be described. The pulley system of drive coupler 240 includes an annular member or a cup 264, a driver pulley 270a, an idler pulley 270b, and a belt 232. Cup 264 is configured to receive surgical instrument 200 (FIG. 2) therein, and transfer its rotational motion to surgical instrument 200 when surgical instrument 200 is received therein. Cup 264 defines a lateral slot or slit 266 therein configured for the lateral passage of shaft 202 of surgical instrument 200.

In some embodiments, cup 264 may act as a replacement for the gear 164 of drive coupler 140 (FIG. 5) and be incorporated into or embedded within internal housing 148 of inner member 144 (FIG. 5). In another embodiment, cup 264 may act as a replacement for the internal housing 148 of inner member 144 (FIG. 5) and assume a similar shape as internal housing 148 of inner member 144.

Driver pulley 270a is configured to be non-rotatably coupled to shaft 130 (FIG. 5) of surgical instrument holder 120 such that rotation of shaft 130, via an actuation of motor 112 of instrument drive unit 110, rotates driver pulley 270a. Idler pulley 270b is spaced from driver pulley 270a, for example, a distance equal to or substantially equal to the diameter of cup 264. Belt 232 of the pulley system has an inner surface 232a wrapped around driver pulley 270a and idler pulley 270b, and an outer surface 232b in frictional engagement with an outer surface 268 of cup 264. As such, a rotation of driver pulley 270a causes drive belt 232 to rotate about pulleys 270a, 270b to effect a rotation of cup 264.

Figure 8:
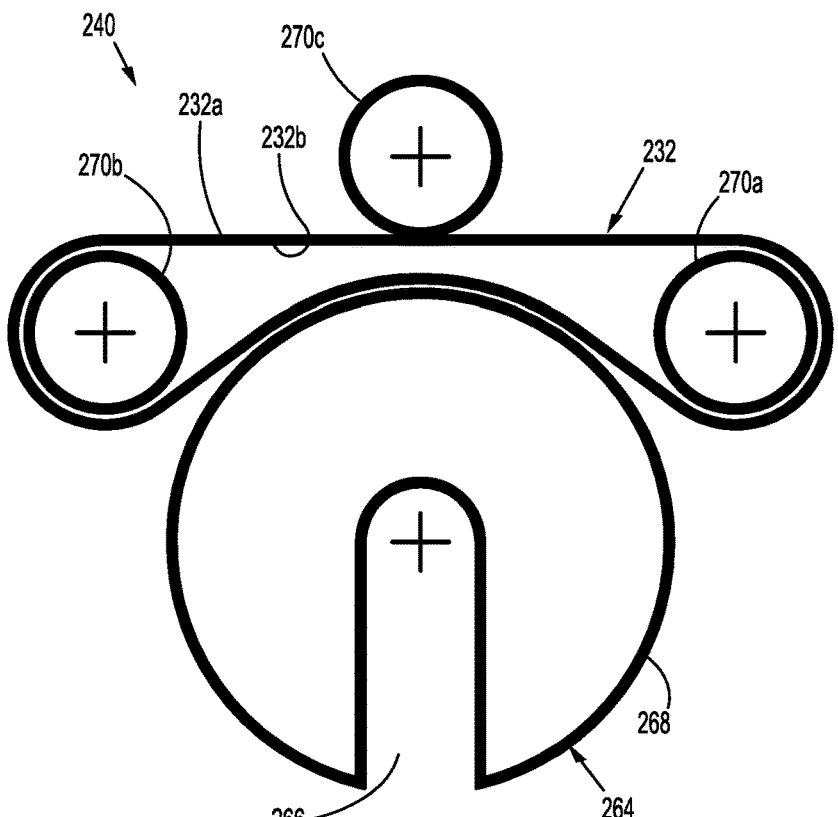
FIG. 8 is a top view of another embodiment of a pulley system configured to be incorporated into the surgical instrument holder of FIG. 4.

With reference to FIG. 8, drive coupler 240 may include a second idler pulley 270c disposed at a location that is equidistant from driver pulley 270a and first idler pulley 270b. Second idler pulley 270c is engaged to outer surface 232b of belt 232 to add tension in belt 232. In some embodiments, second idler pulley 270c may act as an additional driver pulley by being operably coupled to a drive shaft (not shown) of surgical instrument holder 120 to add torque to the pulley system.

Figure 9:
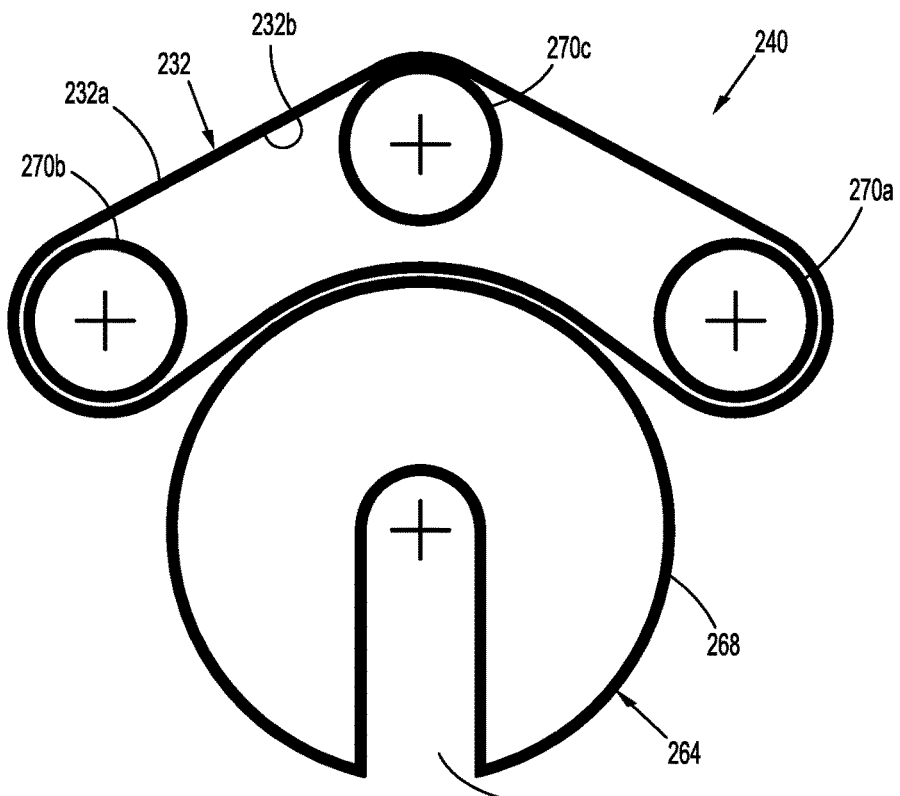
FIG. 9 is yet another embodiment of a pulley system configured to be incorporated into the surgical instrument holder of FIG. 4.

With reference to FIG. 9, instead of second idler pulley 270c being disposed outside of belt 232, idler pulley 270c may be disposed within belt 232 and engaged to inner surface 232a of belt 232 to add tension in belt 232.

The pulley system of FIGS. 7-9 reduces noise, reduces backlash, and provides a lower profile or minimized form factor for the motor drive mechanism placement.

In some embodiments, instrument drive unit 110, or any suitable component thereof, may include position sensors and/or encoders within its drives configured to auto-align and clock instrument drive unit 110 with gear 164 or any suitable component of inner member 144. In some embodiments, instrument drive unit 110 may be mounted onto slide 50 with positions for instrument exchange or for different height or length instrument housings. Instrument drive unit 110 may also incorporate an additional pivot mount (not shown), or there may be a separate, removable device (not shown) that is loaded onto the top of surgical instrument 200 or to provide axial loading access. Instrument drive unit 110 may be sterilized through autoclave, use of an ethylene oxide (ETO) process, use of peroxide, use of gamma radiation or be aseptically placed in a sterilized housing cover or be under a sterile drape with a sterile interface plate. Instrument drive unit 110 can be powered with an external cable or with an internal connector interface.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. A surgical instrument holder, comprising:
an outer member defining a lateral slot therein;
a first annular member defining a lateral slot therein in alignment with the lateral slot of the outer member such that the surgical instrument is receivable within the surgical instrument holder through the lateral slots of the outer member and the first annular member;
a second annular member operably coupled with the first annular member; and
an inner member including:
an internal housing rotatably disposed within the outer member, the internal housing defining a lateral slot therein configured to be in alignment with the lateral slots of the outer member and the first annular member, wherein the second annular member is configured to be drivingly rotated by an instrument drive unit to effect rotation of the internal housing relative to the outer member;
an upper plate fixed to a first side of the internal housing and supported on and extending over an upper surface of the outer member; and
a lower plate fixed to a second side of the internal housing and supported on and extending over a lower surface of the outer member such that the outer member is captured between the upper and lower plates.

2. The surgical instrument holder according to claim 1, further comprising bearings disposed between the upper plate of the inner member and the upper surface of the outer member, and the lower plate of the inner member and the lower surface of the outer member.

3. The surgical instrument holder according to claim 1, wherein the first and second annular members are first and second gears, respectively.

4. The surgical instrument holder according to claim 3, further comprising a pair of gears spaced from one another and in meshing engagement with the first and second gears to transfer rotational motion from the second gear to the first gear.

5. The surgical instrument holder according to claim 4, wherein the lateral slot of the first gear has a width, and wherein the pair of gears are spaced from one another a distance greater than the width of the lateral slot of the first gear.

6. The surgical instrument holder according to claim 1, further comprising:
first and second pulleys spaced from one another and disposed adjacent the first annular member; and
a belt disposed about the first and second pulleys and in engagement with the first annular member, wherein at least one of the first or second pulleys is configured to be drivingly rotated to rotate the belt to effect rotation of the first annular member relative to the outer member.

7. The surgical instrument holder according to claim 1, wherein the internal housing defines a counterbore therein configured for receipt of the surgical instrument therein, the counterbore being in communication with the lateral slot of the first annular member.

8. The surgical instrument holder according to claim 7, wherein the counterbore includes:
a first cavity configured for non-rotatable receipt of a housing of the surgical instrument; and
a second cavity in communication with the first cavity and configured for receipt of a shaft of the surgical instrument.

9. The surgical instrument holder according to claim 1, wherein the first annular member has a passageway extending therethrough in communication with the lateral slot of the first annular member, the passageway configured for receipt of the surgical instrument therein.

10. A surgical assembly for use with a surgical robotic arm, comprising:
a surgical instrument including:
a housing;
a shaft extending distally from the housing and defining a longitudinal axis; and
an end effector coupled to a distal end portion of the shaft;
an instrument drive unit configured for driving an actuation of the end effector of the surgical instrument; and
a surgical instrument holder including:
an outer member defining a lateral slot therein;
a first annular member defining a lateral slot therein in alignment with the lateral slot of the outer member such that the shaft of the surgical instrument is receivable within the surgical instrument holder through the lateral slots of the outer member and the first annular member;
a second annular member operably coupled with the first annular member; and
an inner member including:
an internal housing rotatably disposed within the outer member, the internal housing defining a lateral slot therein configured to be in alignment with the lateral slots of the outer member and the first annular member, wherein the second annular member is configured to be drivingly rotated by the instrument drive unit to effect rotation of the internal housing relative to the outer member, whereby at least the shaft and the end effector of the surgical instrument rotate about the longitudinal axis defined by the shaft;
an upper plate fixed to a first side of the internal housing and supported on and extending over an upper surface of the outer member; and a lower plate fixed to a second side of the internal housing and supported on and extending over a lower surface of the outer member such that the outer member is captured between the upper and lower plates.

11. The surgical assembly according to claim 10, further comprising bearings disposed between the upper plate of the inner member and the upper surface of the outer member, and the lower plate of the inner member and the lower surface of the outer member.

12. The surgical assembly according to claim 10, wherein the first and second annular members are first and second gears, respectively.

13. The surgical assembly according to claim 12, further comprising a pair of gears spaced from one another and in meshing engagement with the first and second gears to transfer rotational motion from the second gear to the first gear.

14. The surgical assembly according to claim 13, wherein the lateral slot of the first gear has a width, and wherein the pair of gears are spaced from one another a distance greater than the width of the lateral slot of the first gear.

15. The surgical assembly according to claim 10, further comprising:
   first and second pulleys spaced from one another and disposed adjacent the first annular member; and
   a belt disposed about the first and second pulleys and in engagement with the first annular member, wherein at least one of the first or second pulleys is configured to be drivingly rotated to rotate the belt to effect rotation of the first annular member relative to the outer member.

16. The surgical assembly according to claim 10, wherein the first annular member has a passageway extending therethrough in communication with the lateral slot of the first annular member, the passageway configured for receipt of the shaft of the surgical instrument therein.

17. A surgical assembly for use with a surgical robotic arm, comprising:
   a surgical instrument including:
      a housing;
      a shaft extending distally from the housing and defining a longitudinal axis; and
      an end effector coupled to a distal end portion of the shaft;
   an instrument drive unit configured for driving an actuation of the end effector of the surgical instrument; and
   a surgical instrument holder including:
      an outer member defining a lateral slot therein;
      a first annular member defining a lateral slot therein in alignment with the lateral slot of the outer member such that the shaft of the surgical instrument is receivable within the surgical instrument holder through the lateral slots of the outer member and the first annular member;
      a second annular member operably coupled with the first annular member; and
      an inner member including:
         an internal housing rotatably disposed within the outer member, the internal housing defining:
            a lateral slot therein configured to be in alignment with the lateral slots of the outer member and the first annular member, wherein the second annular member is configured to be drivingly rotated by the instrument drive unit to effect rotation of the internal housing relative to the outer member, whereby at least the shaft and the end effector of the surgical instrument rotate about the longitudinal axis defined by the shaft; and
            a counterbore therein configured for receipt of the surgical instrument therein, the counterbore being in communication with the lateral slot of the first annular member.

18. The surgical assembly according to claim 17, wherein the counterbore includes:
   a first cavity configured for non-rotatable receipt of the housing of the surgical instrument; and
   a second cavity in communication with the first cavity and configured for receipt of the shaft of the surgical instrument.

* * * * *